US008882769B2

(12) United States Patent
Gupta

(10) Patent No.: US 8,882,769 B2
(45) Date of Patent: Nov. 11, 2014

(54) PLATE SYSTEM FOR MANAGING A BONE FRACTURE

(76) Inventor: Amit Gupta, Prospect, KY (US)

( * ) Notice: Subject to any disclaimer, the term of this patent is extended or adjusted under 35 U.S.C. 154(b) by 346 days.

(21) Appl. No.: 13/163,594

(22) Filed: Jun. 17, 2011

(65) Prior Publication Data

US 2011/0319894 A1 Dec. 29, 2011

Related U.S. Application Data

(60) Provisional application No. 61/358,558, filed on Jun. 25, 2010.

(51) Int. Cl.

| | |
|---|---|
| ***A61B 17/56*** | (2006.01) |
| ***A61B 17/58*** | (2006.01) |
| ***A61B 17/80*** | (2006.01) |
| ***A61F 2/30*** | (2006.01) |
| ***F04D 29/66*** | (2006.01) |
| ***F04D 25/06*** | (2006.01) |
| ***F04D 29/42*** | (2006.01) |

(52) U.S. Cl.

CPC .......... *F04D 25/0613* (2013.01); *F04D 29/667* (2013.01); *F04D 29/422* (2013.01)

USPC .................. 606/70; 60/282; 60/286; 60/308; 60/310

(58) Field of Classification Search

USPC .................................................. 606/280–299

See application file for complete search history.

(56) References Cited

U.S. PATENT DOCUMENTS

| | | | | |
|---|---|---|---|---|
| 7,137,987 | B2 | 11/2006 | Patterson et al. | |
| 7,335,204 | B2 | 2/2008 | Tornier | |
| 2004/0102775 | A1* | 5/2004 | Huebner | 606/69 |
| 2005/0075633 | A1* | 4/2005 | Ross | 606/61 |
| 2005/0182405 | A1 | 8/2005 | Orbay et al. | |
| 2010/0256687 | A1 | 10/2010 | Neufeld et al. | |
| 2011/0282389 | A1* | 11/2011 | Janice et al. | 606/264 |
| 2012/0123484 | A1* | 5/2012 | Lietz et al. | 606/281 |
| 2012/0203228 | A1* | 8/2012 | Raven et al. | 606/70 |

OTHER PUBLICATIONS

ISA/KR, International Search Report and Written Opinion for corresponding international application PCT/US2011/040978, completed Feb. 16, 2012.

* cited by examiner

*Primary Examiner* — Andrew Yang
*Assistant Examiner* — Olivia C Chang
(74) *Attorney, Agent, or Firm* — Stites & Harbison, PLLC; David W. Nagle, Jr.

(57) ABSTRACT

A plate system is used in a surgical procedure to manage a distal radius or similar bone fracture. A plate of the plate system includes two leg segments extending downwardly from a generally horizontal segment, and further includes an elongated slot defined through the center of the horizontal segment of the plate near its top edge. A subchondral support element is inserted through the elongated slot and is advanced into the bone. The plate further defines two holes through the horizontal segment near a respective one of the two leg segments. Locking screws, such as variable angle locking screws, are inserted into and locked into the respective holes, with each locking screw advancing into the bone such that a distal tip of each locking screw engages the subchondral support element, thus providing a three-point support.

30 Claims, 13 Drawing Sheets

120
81
10a
8
80a
8
80
82a
82
88
90
10b

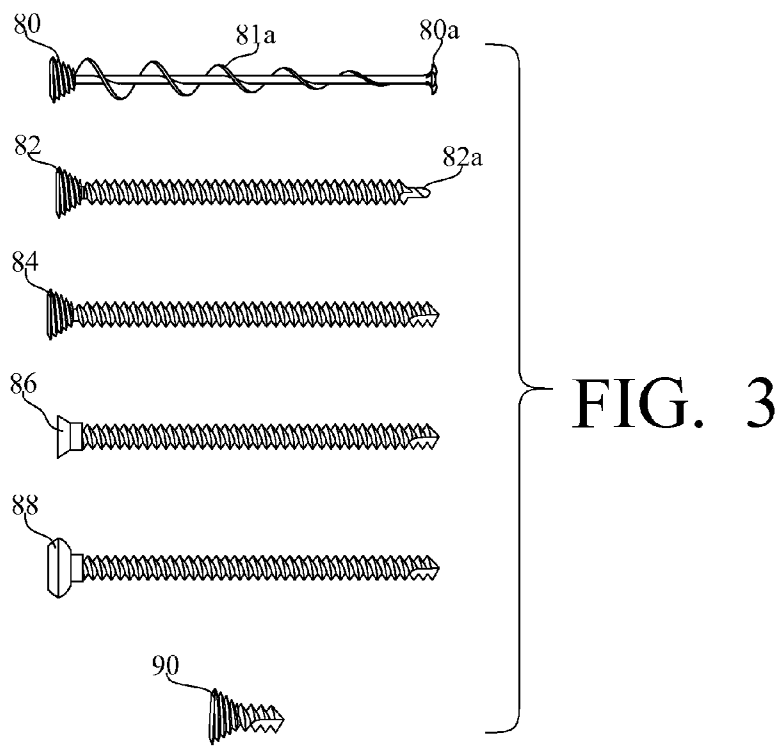
FIG. 3
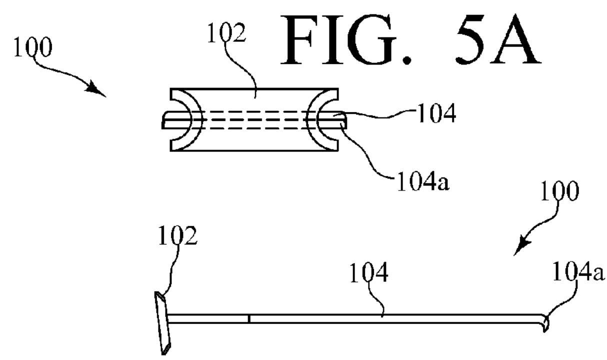
FIG. 5A
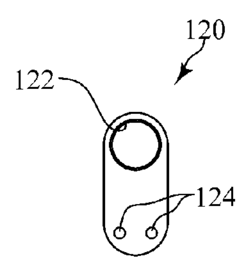
FIG. 4A
FIG. 5B
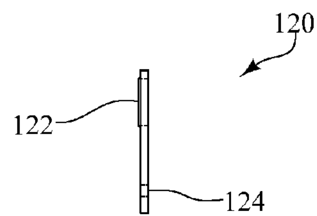
FIG. 4B
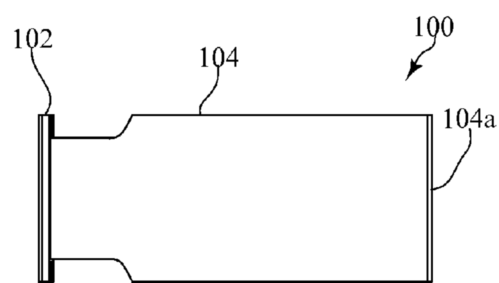
FIG. 5C 10a
90
20
10b
124
90
32
120
120
34
26a
24a
26
24
42a
62a
88
102
82
82
88
42
62
40
60
90
90
10
50
52

100
104
104a
120
90
82a
82
88
90
10a
10b

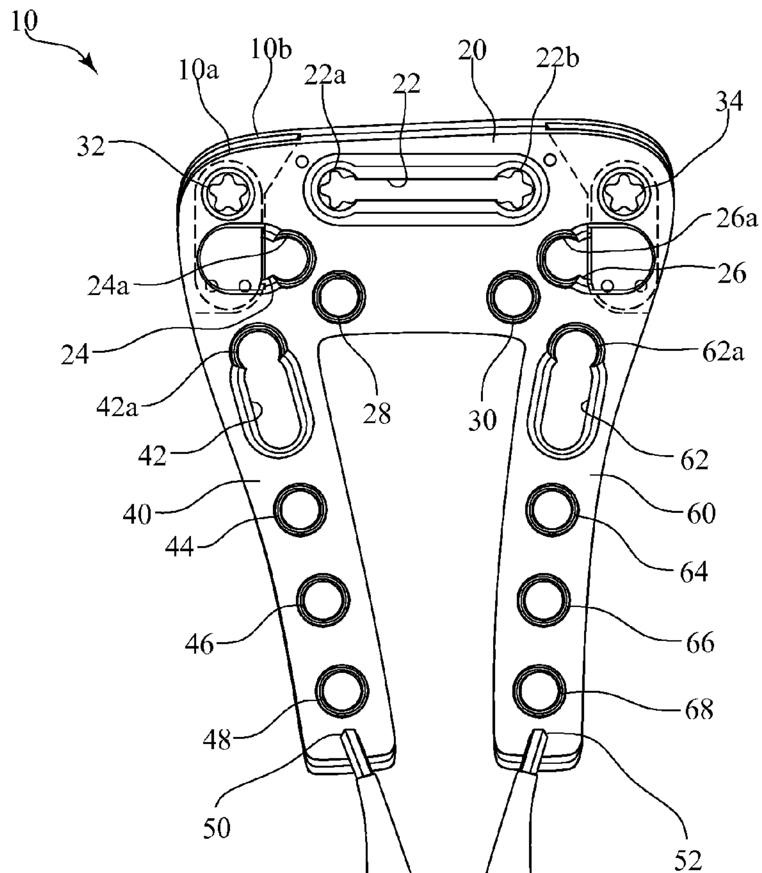
FIG. 13
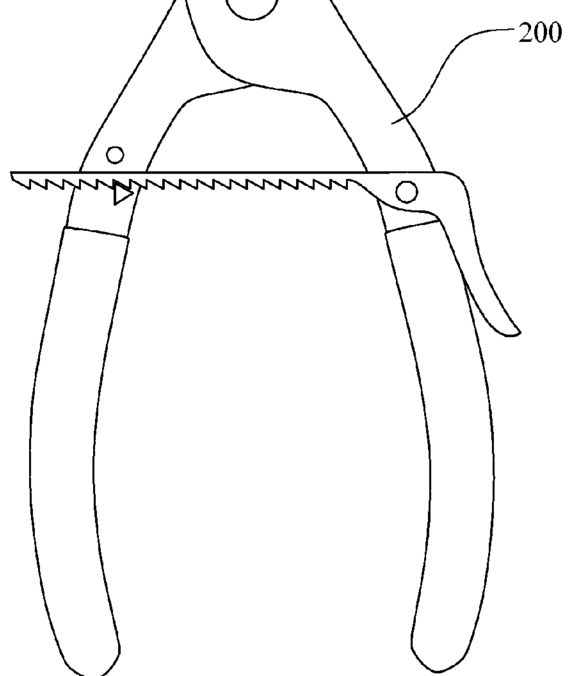

PLATE SYSTEM FOR MANAGING A BONE FRACTURE

CROSS-REFERENCE TO RELATED APPLICATIONS

The present application claims priority to U.S. Provisional Patent Application Ser. No. 61/358,558 filed on Jun. 25, 2010, the entire disclosure of which is incorporated herein by reference.

BACKGROUND OF THE INVENTION

The present invention pertains to the management of a bone fracture, and, more particularly, a plate system that is used in a surgical procedure to manage a distal radius or similar bone fracture.

A distal radius fracture is a bone fracture of the radius in the forearm, and indeed, it is one of the most common bone fractures. Because of its proximity to the wrist joint, such a fracture is often referred to as a wrist fracture.

The management of distal radius fractures has evolved through many phases. In the 1950s and 1960s, closed reduction and immobilization (i.e., casting) were preferred forms of treatment. Unfortunately, in a large proportion of displaced distal radius fractures, casting was unable to maintain the alignment of the fragments and the reduction. Therefore, percutaneous pinning was added as an adjunct, and many variations of percutaneous pinning techniques were used.

In the 1980s, the management of distal radius fractures was mostly through external fixation. Many types of external fixation techniques were developed and used, including mobile external fixation systems. In addition to the external fixation, percutaneous fixation was also used in some circumstances.

In the 1990s, the trend shifted toward internal fixation, where a plate was applied to the dorsal surface of the radius. Although this form of internal fixation was generally successful, there were many problems with placement of thick metal plates on the dorsal surface of the radius where there was very little space for a plate. For instance, there were many reports of tendonitis and tendon rupture due to such plates rubbing against the tendons.

In the 2000s, the trend shifted toward placing the plate on the palmar surface of the radius—volar (palmar) radial plating. The palmar surface of the radius is relatively flat and is able accommodate a plate under the thick pronator quadratus muscle that covers this surface. In placing the plate on the palmar surface of the radius, early screws that were utilized were non-locking screws. Later, locking screws were used that allowed for an angle stable fixation of the distal radius fracture, thus providing a very stable construct. Then, in order to address complex intraarticular fractures, variable angle locking screws were designed and utilized. Thus, currently available radial plates have either fixed or variable angle locking screws or pegs in one or two columns on a horizontal segment of the plate, and non-locking or locking bicortical screws on a single central vertical segment of the plate.

Still, the management of distal radius fractures continues to evolve, and it would be desirable to provide a plate system that results in a very stable and robust support, which can be used not only for a distal radius fracture, but also for fractures in other bones.

SUMMARY OF THE INVENTION

The present invention is a plate system that is used in a surgical procedure to manage a distal radius or similar bone fracture. The plate includes two leg segments extending downwardly from a generally horizontal segment, and further includes an elongated slot defined through the center of the horizontal segment of the plate near its top edge. A subchondral support element is inserted through the elongated slot and advanced into the bone. The plate further defines two holes through the horizontal segment near a respective one of the two leg segments. Locking screws, such as variable angle locking screws, are inserted into and locked into the respective holes, with each locking screw advancing into the bone such that a distal tip of each locking screw engages the subchondral support element, thus providing a “kickstand” effect and a robust three-point and subchondral support that is particularly beneficial for managing simple intraarticular fractures and extraarticular fractures in osteoporotic bones.

In one exemplary embodiment, the plate has a generally horseshoe-like shape with the two leg segments extending downwardly from the generally horizontal segment. There is an elongated slot defined through the center of the horizontal segment of the plate near the top edge, with variable angle locking holes at either end of the elongated slot. There are also two threaded holes defined through the horizontal segment near the two leg segments. There are also two additional elongated slots defined through the horizontal segment of the plate, one near the left edge of the plate and one near the right edge of the plate, with threaded portions at the inside ends of each elongated slot.

Additionally, there is an elongated slot defined through and aligned with one leg segment, and there is an identical elongated slot defined through and aligned with the other leg segment. Each elongated slot has a threaded portion at its upper end. Furthermore, there are threaded holes defined through one leg segment along the length of the leg segment, along with threaded holes defined through the other leg segment along the length of the other leg segment.

In one implementation and use of the plate system of the present invention, the plate is positioned against and secured to the distal radius (or other bone) to provide stability to a fracture. A paddle screw with an auger-like flight is inserted into each end of the elongated slot defined through the center of the horizontal segment of the plate, and then is advanced into the bone, with the paddle screws serving as the subchondral support element. Furthermore, in this implementation and use, the head of each paddle screw can be locked into the respective variable angle locking holes at either end of the elongated slot. Also, the distal end of the paddle screw has a number of paddles that collectively define a surface at its distal end. A locking screw is inserted through each of the threaded holes defined through the horizontal segment, and each locking screw is advanced into the bone with the distal tip of each locking screw engaging one or more of the paddles at the distal end of the respective paddle screw. The result is that each paddle screw and associated locking screw, which are both locked to the plate, make contact on the far side of the subchondral and subcortical space of the radius, thus providing a “kickstand” effect and a robust three-point and subchondral support.

In another implementation and use of the plate system of the present invention, certain screws are oriented to provide a “kickstand” subchondral support system in combination with a thin metal blade assembly that is positioned in the subchondral space. An exemplary metal blade assembly generally comprises a blade that is a substantially flat plate, but terminates in a curved distal edge. At the opposite end of the blade, there is a substantially perpendicular front plate. As a result of this construction, the blade can be inserted into the elongated slot defined through the center of the horizontal segment of the plate near its top edge. Then, a locking screw is inserted through each of the threaded holes defined through the horizontal segment, and each locking screw is then advanced into the bone with the distal tip of each locking screw engaging the curved distal edge of the blade. Thus, the blade and the variable angle locking screws collectively provide the "kickstand" effect and a robust three-point and subchondral support.

In some implementations and uses of the plate system of the present invention, non-locking screws are also inserted through each of the elongated slots aligned with the leg segments and then advanced into the bone. These non-locking screws help secure the plate to the bone and are used as the initial fixation screws. Having one locking screw and associated elongated slot on either side makes it possible to fine tune the tilt and height of the plate relative to the bone. As mentioned above, the elongated slots are also provided with threaded portions at the upper ends of each elongated slot, which can accommodate locking screws if needed.

In some implementations and uses of the plate system of the present invention, unicortical locking screws are also inserted into each of the threaded holes defined through the respective leg segments of the plate. Each of these unicortical locking screws is locked into the plate at a fixed angle.

As a further refinement, the additional elongated slots defined through the horizontal segment of the plate can also accommodate additional non-locking screws. Such non-locking screws can be used: (i) to pull the fracture fragment to the plate, thus finely reducing the fracture and preventing the plate from standing off of the bone as can happen when only locking screws are used and the fracture is incompletely reduced; (ii) as lag screws for large intraarticular fractures such as a coronal split of the lunate fossa (Malone Type IV fracture); and (iii) to compress a radial fragment and an ulnar fragment by virtue of eccentrically placed screws. Typically, such non-locking screws would be bicortical and would be inserted into the distal fracture fragment.

As a further refinement, the plate may also include two variable angle locking holes, one near the extreme radial (or left) edge of the plate and one near the extreme ulnar (or right) edge of the plate. A rotating tab engages and rotates with respect to each of these variable angle locking holes. In a first or down position, each rotating tab provides volar support for the head of a non-locking screw that is received in one of the elongated slots defined through the horizontal segment of the plate. In other words, the head of each non-locking screw can be covered by a respective rotating tab in the down position, thus preventing the backing out of the non-locking screw and effectively converting it into a "pseudo" locking mode. In a second or up position, each rotating tab can provide supplementary support to any ulnar or radial styloid fragment that may otherwise not be captured by the plate. In this regard, each rotating tab is provided with holes near its upper edge for accommodating Kirschner wires or small screws.

As a further refinement, the plate may also be provided with hexagonal or other holes near its lower edge that can engage hexagonal protrusions of custom-designed ratchet pliers for pulling the two leg segments toward each other and the central axis of the bone.

DESCRIPTION OF THE DRAWINGS

FIG. 3 includes views of various screws used with the exemplary plate of FIG. 1;

FIG. 4A is a view of a rotating tab that is incorporated into the exemplary plate of FIG. 1;

FIG. 4B is a side view of the rotating tab of FIG. 4A;

FIG. 5A is a front view of an exemplary metal blade assembly for use in one implementation of the plate system of the present invention;

FIG. 5B is a side view of the exemplary metal blade assembly of FIG. 5A;

FIG. 5C is a top view of the exemplary metal blade assembly of FIG. 5A;

FIG. 13 is a view of a set of ratchet pliers for use with the plate system of the present invention;

DETAILED DESCRIPTION OF THE INVENTION

The present invention is a plate system that is used in a surgical procedure to manage a distal radius or similar bone fracture. The plate includes two leg segments extending downwardly from a generally horizontal segment, and further includes an elongated slot defined through the center of the horizontal segment of the plate near its top edge. A subchondral support element is inserted through the elongated slot and advanced into the bone. The plate further defines two holes through the horizontal segment near a respective one of the two leg segments. Locking screws, such as variable angle locking screws, are inserted into and locked into the respective holes, with each locking screw advancing into the bone such that a distal tip of each locking screw engages the subchondral support element, thus providing a "kickstand" effect and a robust three-point and subchondral support that is particularly beneficial for managing simple intraarticular fractures and extraarticular fractures in osteoporotic bones.

Figure 1:
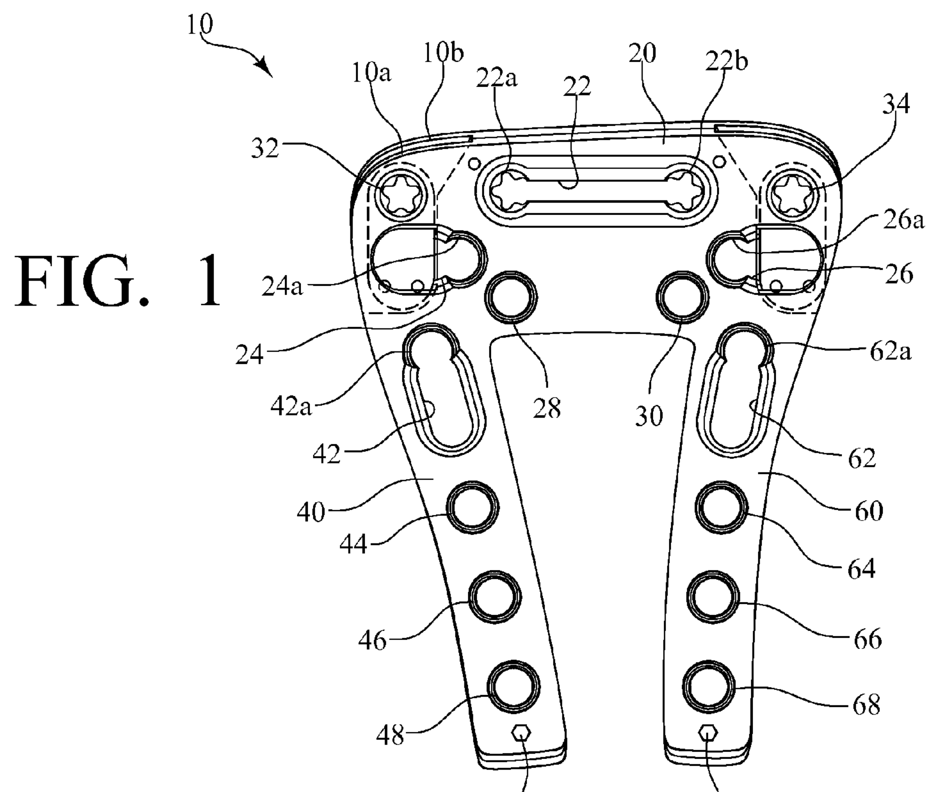
FIG. 1 is a view of an exemplary plate for use in the plate system of the present invention.

Referring now to FIG. 1, in one exemplary embodiment, the plate 10 has a generally horseshoe-like shape with two leg segments 40, 60 extending downwardly from a generally horizontal segment 20. Such a shape with two columns keeps the central area of the bone (i.e., between the leg segments 40, 60) free and accessible. It is also believed that it is much easier to align the ends of the plate 10 to the edges of the bone, thereby obtaining a better centered construct. Furthermore, and as further discussed below, by having two columns, unicortical locking screws can be used to secure the plate 10 to the bone as twice the number of screws can be used as compared to a prior art plate with a single central vertical segment.

Referring still to FIG. 1, there is an elongated slot 22 defined through the center of the horizontal segment 20 of the plate 10 near the top edge, with variable angle locking holes 22*a*, 22*b* at either end of the elongated slot 22. There are also two threaded holes 28, 30 defined through the horizontal segment 20 near the two leg segments 40, 60. There are also two additional elongated slots 24, 26 defined through the horizontal segment 20 of the plate 10, one near the left edge of the plate 10 and one near the right edge of the plate 10, with threaded portions 24*a*, 26*a* at the inside ends of each elongated slot 24, 26. The importance of these elongated slots 22, 24, 26 and threaded holes 28, 30 is discussed in further detail below.

Additionally, referring still to FIG. 1, there is an elongated slot 42 defined through and aligned with one leg segment 40, and there is an identical elongated slot 62 defined through and aligned with the other leg segment 60. Each elongated slot 42, 62 has a threaded portion 42*a*, 62*a* at its upper end. Furthermore, there are threaded holes 44, 46, 48 defined through one leg segment 40 along the length of the leg segment 40, as well as threaded holes 64, 66, 68 defined through the other leg segment 60 along the length of the other leg segment 60. The importance of these elongated slots 42, 62 and threaded holes 44, 46, 48, 64, 66, 68 is also discussed in further detail below.

Figure 2:
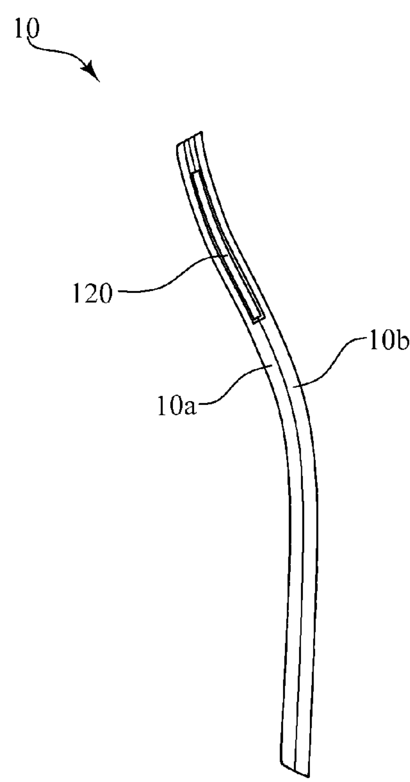
FIG. 2 is a side view of the exemplary plate of FIG. 1.

Referring now to FIG. 2, it should also be noted that the plate 10 has a curvature that mimics the curvature of the distal radius, so that it can be placed against and engage the bone, as is also discussed in further detail below.

Furthermore, in this exemplary embodiment and as shown in FIG. 2, the plate 10 is actually comprised of two sections 10*a*, 10*b* that are joined together, with a cavity defined between the two sections 10*a*, 10*b* on either side of the plate 10 for accommodating a rotating tab 120, which is discussed below.

FIG. 3 shows multiple screws that are used with the plate 10 of FIGS. 1 and 2. The first screw is a "paddle" screw 80, in that it has a number of paddles 80*a* that collectively define a surface at its distal end. This paddle screw 80 also has an auger-like flight 81 that is tapered from the head of the paddle screw 80 to its distal end. The second screw is a variable angle locking screw 82 with a drill-like distal tip 82*a*. The third screw is another variable angle locking screw 84. The fourth and fifth screws are non-locking screws 86, 88. The sixth and final screw is a unicortical locking screw 90. The use and function of these various screws 80, 82, 84, 86, 88, 90 is also discussed in further detail below.

Figure 6:
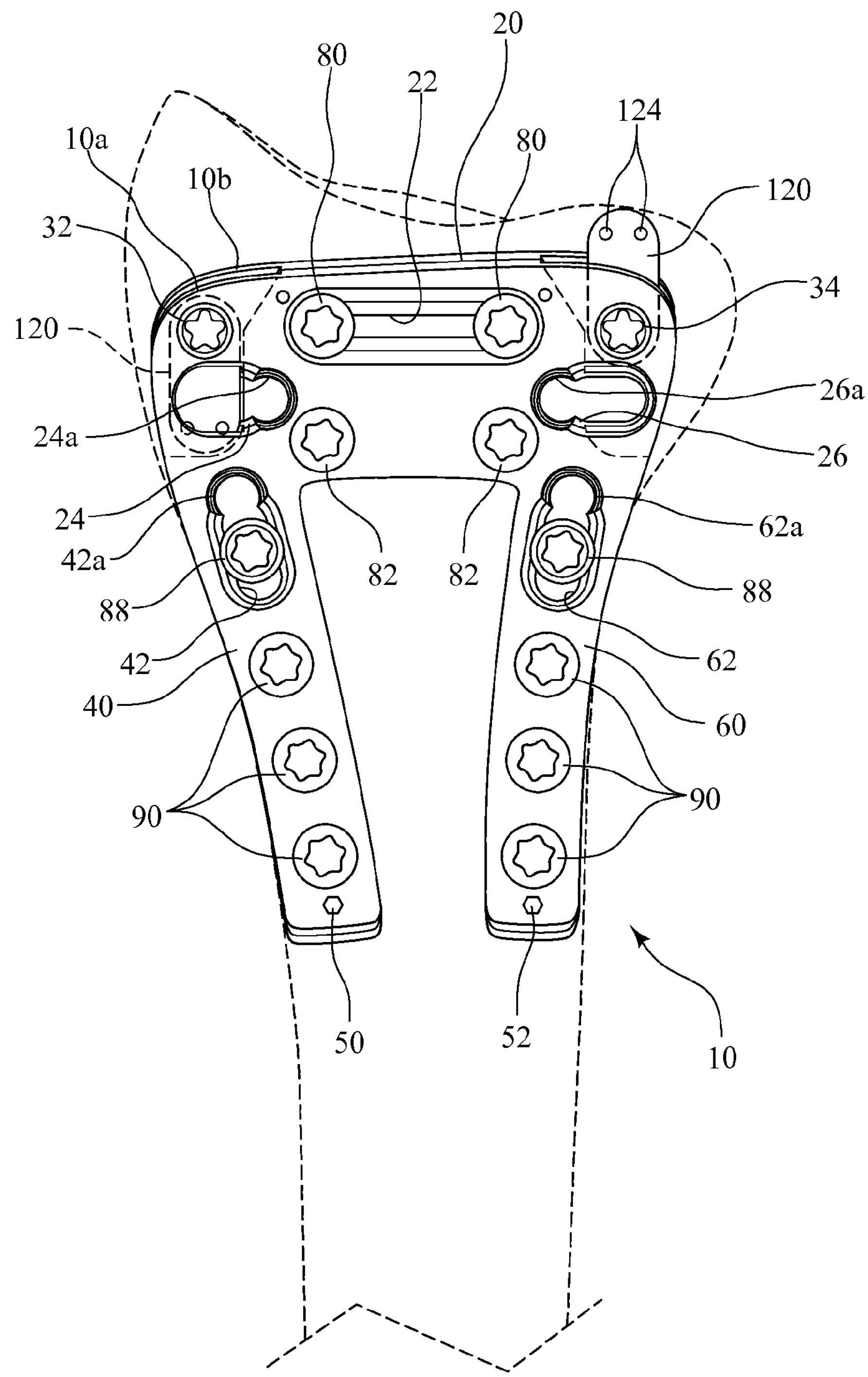
FIG. 6 is a view of the exemplary plate of FIG. 1 secured to a radius.
Figure 7:
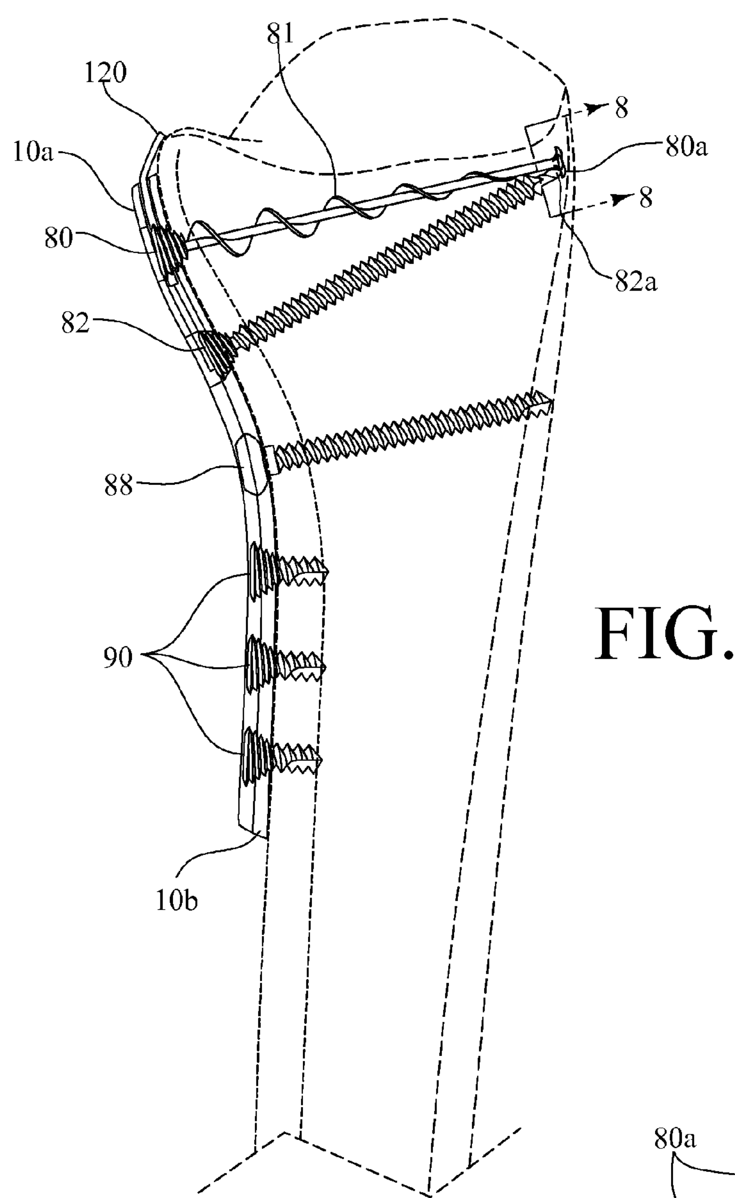
FIG. 7 is a side sectional view of the exemplary plate of FIG. 6 as secured to the radius.
Figure 8:
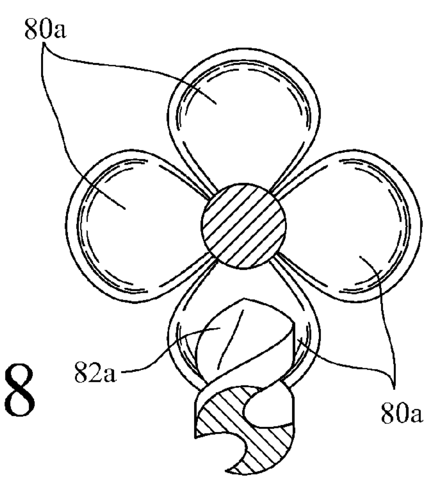
FIG. 8 is a view taken along line 8-8 of FIG. 7.

Referring now to FIGS. 6-8, in one implementation and use of the plate system of the present invention, the plate 10 is positioned against and secured to the distal radius (or other bone) to provide stability to a fracture. In this implementation, certain screws are oriented to provide a "kickstand" subchondral support system (which may be referred to by the acronym KISS). Specifically, a paddle screw 80 with the auger-like flight 81 is inserted into each end of the elongated slot 22 defined through the center of the horizontal segment 20 of the plate 10, and then advanced into the bone. Thus, in this implementation and use of the plate system of the present invention, the paddle screws 80 serve as the subchondral support element.

Furthermore, in some implementations and uses of the plate system of the present invention, the head of each paddle screw 80 can be locked into the respective variable angle locking holes 22*a*, 22*b* at either end of the elongated slot 22. Also, as best shown in FIG. 8 and as mentioned above, the distal end of the paddle screw 80 has a number of paddles 80*a* that collectively define a surface at its distal end. A variable angle locking screw 82 (having a drill-like distal tip 82*a* in this example) is inserted through each of the threaded holes 28, 30 defined through the horizontal segment 20, and each variable angle locking screw 82 is advanced into the bone with the distal tip 82*a* of each variable angle locking screw 82 engaging one or more of the paddles 80*a* at the distal end of the respective paddle screw 80. Of course, as an alternative, the screw could be provided with a conical or other structure at its distal end (instead of paddles) to provide an engagement surface for the distal tip 82*a* of the variable angle locking screw 82. In any event, and as best shown in FIG. 7, the result is that each paddle screw 80 and the associated variable angle locking screw 82, which are both locked to the plate 10, make contact on the far side of the subchondral and subcortical space of the radius, thus providing a "kickstand" effect and a robust three-point and subchondral support. Such an arrangement is particularly beneficial for managing simple intraarticular fractures and extraarticular fractures in osteoporotic bones.

Also, with respect to FIGS. 6-8, in some implementations and uses of the plate system of the present invention, non-locking screws 88 are inserted through each of the elongated slots 42, 62 aligned with the respective leg segments 40, 60 and then advanced into the bone. These non-locking screws 88 help secure the plate 10 to the bone and are used as the initial fixation screws. Also, having one locking screw 88 and associated elongated slot 42, 62 on either side makes it possible to fine tune the tilt and height of the plate 10 relative to the bone. As mentioned above, the elongated slots 42, 62 are also provided with threaded portions 42*a*, 62*a* at the upper ends of each elongated slot 42, 62, which can accommodate locking screws if needed.

Finally, with respect to FIGS. 6-8, in some implementations and uses of the plate system of the present invention, a unicortical locking screw 90 is inserted into each of the threaded holes 44, 46, 48, 64, 66, 68 defined through the respective leg segments 40, 60 of the plate 10. Each of these unicortical locking screws 90 is locked into the plate 10 at a fixed angle. Furthermore, it is believed that using six unicortical locking screws 90, as opposed to fewer bicortical locking screws (as in prior art systems), will provide for similar strength; however, the advantage of unicortical locking screws is that there is less risk of dorsal structure irritation with mistakenly applied long screws. Moreover, there will be space for a plate and screws on the dorsal side should there be a need for that type of fixation.

Figure 9:
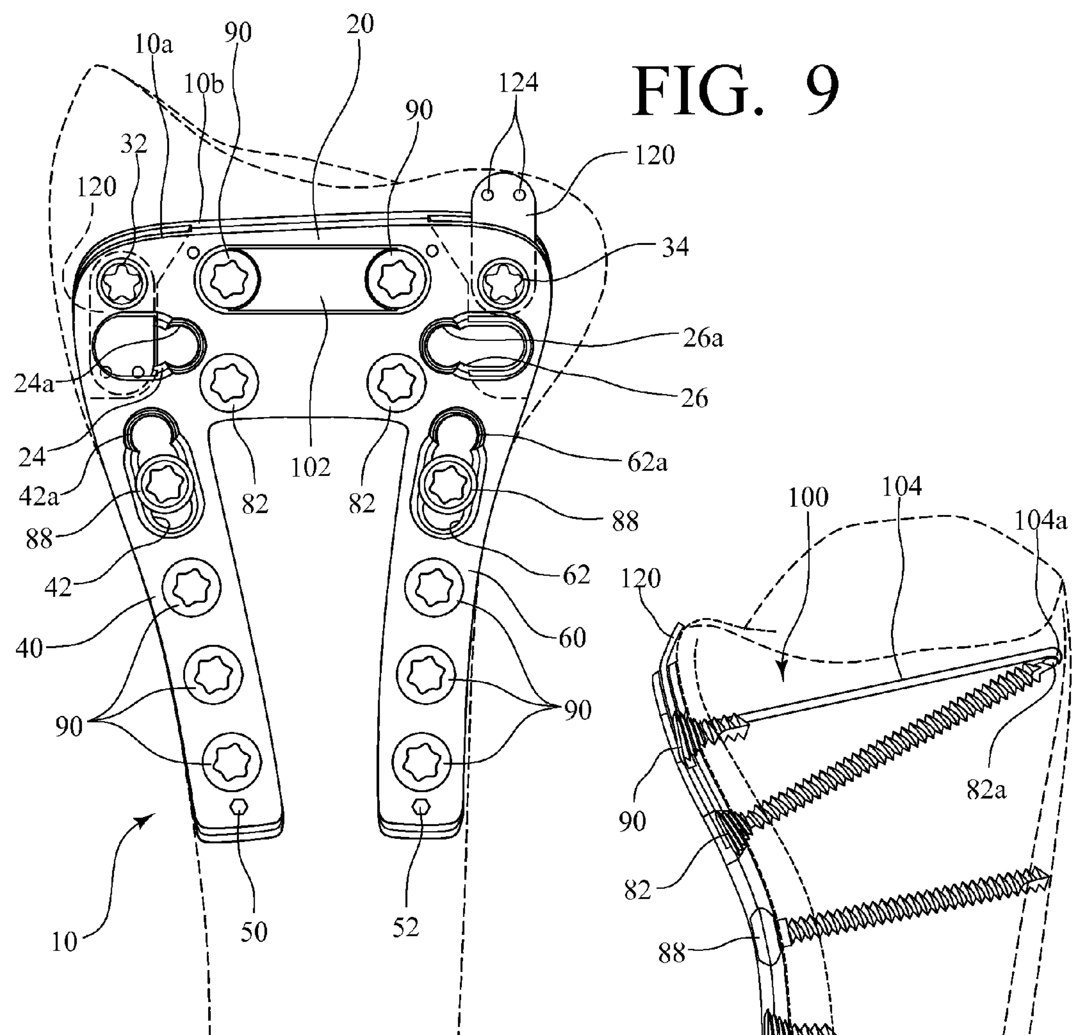
FIG. 9 is a view of the exemplary plate of FIG. 1 secured to a radius in a manner similar to that shown in FIG. 6, but with one rotating tab rotated to the up position.
Figure 10:
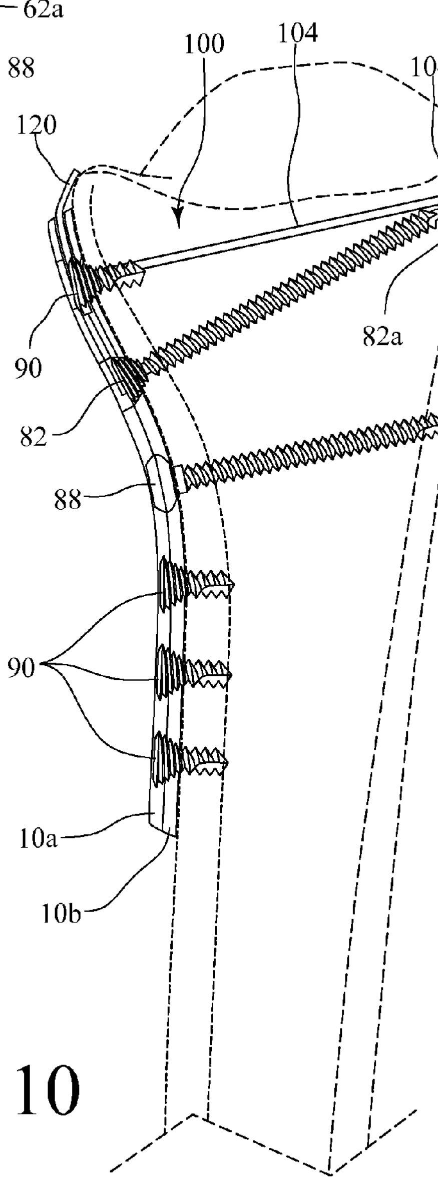
FIG. 10 is a side sectional view of the exemplary plate of FIG. 9 as secured to the radius.

FIGS. 9-10 illustrate another implementation and use of the plate system of the present invention, which is particularly useful for managing a comminuted intraarticular fracture, especially when there is a central "die-punch" or depression fracture. In this implementation, certain screws are oriented to provide a "kickstand" subchondral support system in combination with a thin metal blade assembly that is positioned in the subchondral space. FIGS. 5A-5C are various views of an exemplary metal blade assembly 100, which serves as the subchondral support element. As shown, the exemplary metal blade assembly 100 generally comprises a blade 104 that is a substantially flat plate, but terminates in a curved distal edge 104*a*. At the opposite end of the blade 104, there is a substantially perpendicular front plate 102. As a result of this construction, the blade 104 can be inserted into the elongated slot 22 defined through the center of the horizontal segment 20 of the plate 10 near its top edge, as shown in FIGS. 9-10. Then, a variable angle locking screw 82 (again having a drill-like distal tip 82*a* in this example) is inserted through each of the threaded holes 28, 30 defined through the horizontal segment

20, and each variable angle locking screw 82 is then advanced into the bone with the distal tip 82*a* of each variable angle locking screw 82 engaging the curved distal edge 104*a* of the blade 104. Thus, the blade 104 and the variable angle locking screws 82 collectively provide the "kickstand" effect and a robust three-point and subchondral support similar to that provided in the implementation discussed above with respect to FIGS. 6-8.

Furthermore, in the exemplary implementation and use illustrated in FIGS. 9-10, a unicortical locking screw 90 is inserted into each of the variable angle locking holes 22*a*, 22*b* at either end of the elongated slot 22, thus securing and maintaining the position of the metal blade assembly 100 relative to the plate 10.

Although, in the above exemplary implementations, the plate system of the present invention is used for management of a distal radius fracture, such a kickstand subchondral support system (KISS) may also have applicability for management of fractures in other bones where articular collapse fractures are encountered, including, for example, in the upper tibia, in the distal tibia (pilon fractures), in the proximal and distal humerus, in the radial head along with proximal and distal ulna, and also in the hip region.

Figure 11:
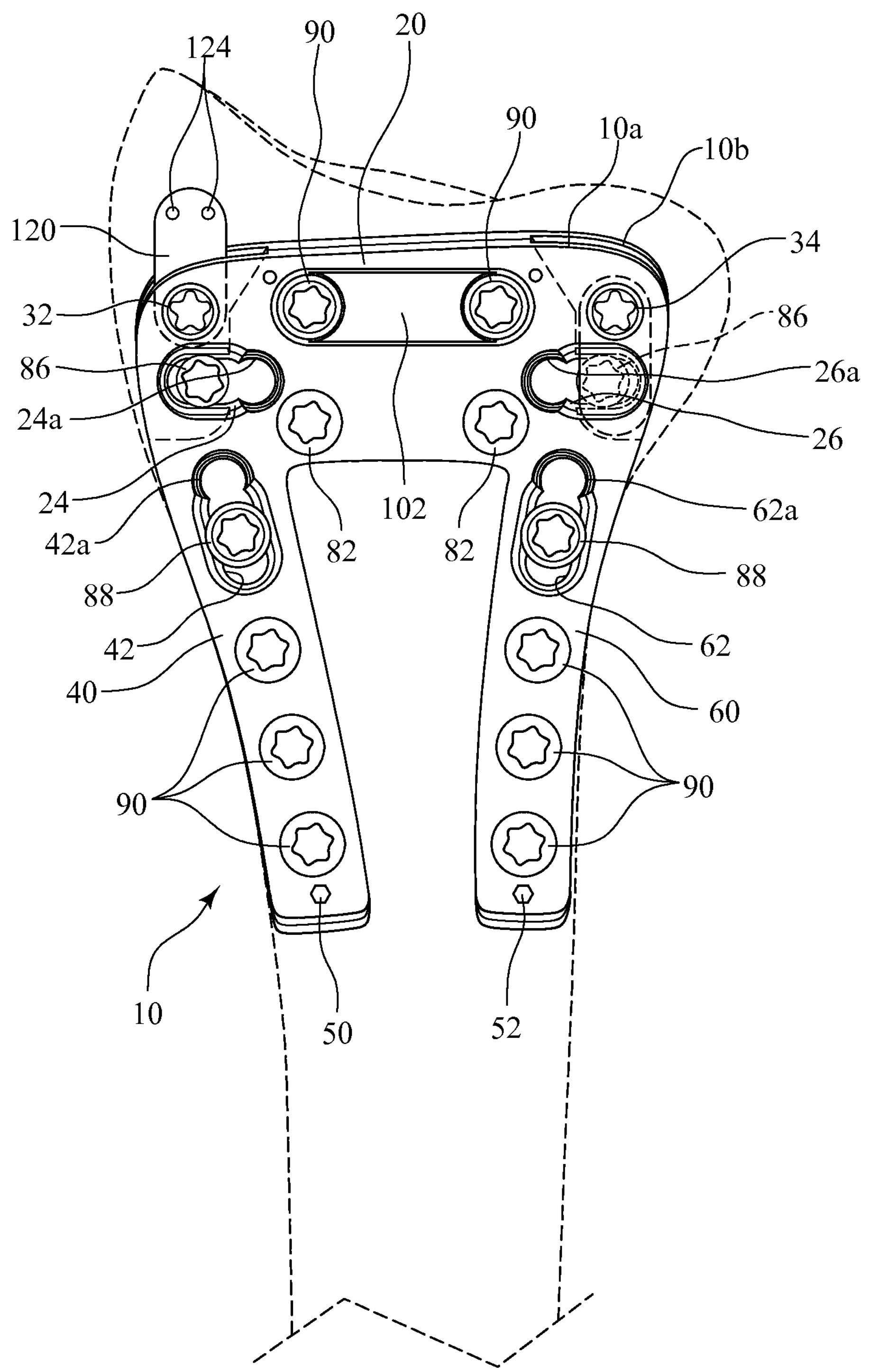
FIG. 11 is a view of the exemplary plate of FIG. 1 secured to a radius in a manner similar to that shown in FIG. 9, but using the exemplary metal blade assembly of FIG. 5A.
Figure 12:
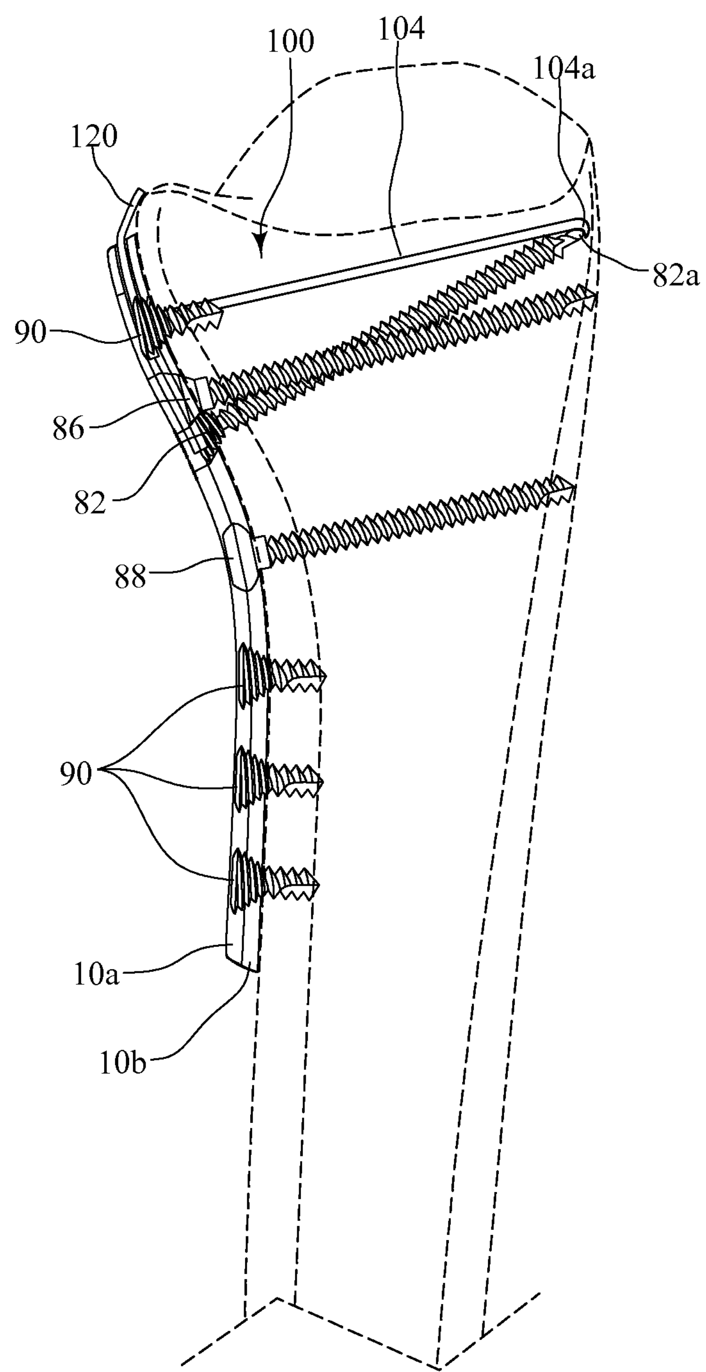
FIG. 12 is a side sectional view of the exemplary plate of FIG. 11 as secured to the radius.

As a further refinement, the additional elongated slots 24, 26 defined through the horizontal segment 20 of the plate can also accommodate additional non-locking screws 86, as shown in FIGS. 11-12. Such non-locking screws 86 can be used: (i) to pull the fracture fragment to the plate 10, thus finely reducing the fracture and preventing the plate 10 from standing off of the bone as can happen when only locking screws are used and the fracture is incompletely reduced; (ii) as lag screws for large intraarticular fractures such as a coronal split of the lunate fossa (Malone Type IV fracture); and (iii) to compress a radial fragment and an ulnar fragment by virtue of eccentrically placed screws. Typically, such non-locking screws 86 would be bicortical and would be inserted into the distal fracture fragment.

As a further refinement, the plate 10 shown in FIGS. 1 and 2 also includes two variable angle locking holes 32, 34, one near the extreme radial (or left) edge of the plate 10 and one near the extreme ulnar (or right) edge of the plate 10. Each of these two variable angle locking holes 32, 34 can accommodate additional locking screws, if needed. A rotating tab 120, as shown in FIGS. 4A and 4B, engages and rotates with respect to each of these variable angle locking holes 32, 34. In this regard, each rotating tab 120 has a raised circumferential lip 122 that fits in and engages one of the variable angle locking holes 32, 34. Furthermore, and as mentioned above, there is a cavity defined between the two sections 10*a*, 10*b* of the plate 10 on either side of the plate 10 for accommodating each rotating tab 120. Each rotating tab 120 can rotate approximately 210° within its respective cavity. In a first or down position, each rotating tab 120 can provide volar support for the head of a non-locking screw 86 that is received in one of the elongated slots 24, 26 defined through the horizontal segment 20 of the plate 10, for example, as shown in the elongated slot 26 in FIGS. 11 and 12. In other words, the head of each non-locking screw 86 can be covered by a respective rotating tab 120 in the down position, thus preventing the backing out of the non-locking screw 86 and effectively converting it into a "pseudo" locking mode. In a second or up position, each rotating tab 120 can provide supplementary support to any ulnar or radial styloid fragment that may otherwise not be captured by the plate 10. In this regard, each rotating tab 120 is provided with holes 124 (as shown in FIG. 5) near its upper edge for accommodating Kirschner wires or small screws. Such use of the rotating tabs 120 can be particularly important for a volar ulnar fragment that is notoriously missed in a standard volar plate fixation.

As a further refinement, with respect to the elongated slots 24, 26 defined through the horizontal segment 20 of the plate 10, as mentioned above, there are threaded portions 24*a*, 26*a* at the inside ends of each elongated slot 24, 26. Although not shown in the Figures, these threaded portions 24*a*, 26*a* can receive a locking screw, such as bicortical locking screw, to provide supplemental fixation. This may be of particular importance when the associated rotating tab 120 is in a second or up position, and thus can not be used to prevent the backing out of the non-locking screw 86.

As a further refinement, the plate 10 may be provided with hexagonal or other holes near its lower edge that can engage hexagonal protrusions of custom-designed ratchet pliers 200, as shown in FIG. 13. Such ratchet pliers 200 would be used to pull the two leg segments 40, 60 toward each other and the central axis of the bone.

With respect to the exemplary plate 10 described above with reference to FIGS. 1-13, the generally horizontal segment 20 of the exemplary plate 10 can thus be characterized as having three rows. The elongated slot 22, including the variable angle locking holes 22*a*, 22*b*, and the variable angle locking holes 32, 34 are in the first (or upper) row. The two additional elongated slots 24, 26 are in the second (or middle) row. The threaded holes 28, 30 are in the third (or lower) row.

With respect to the exemplary plate 10 described above with reference to FIGS. 1-13, an exemplary method for managing a fracture of a bone in accordance with the present invention comprises the steps of: providing a plate with two leg segments extending downwardly from a generally horizontal segment, said plate further including an elongated slot defined through the generally horizontal segment near its top edge, and two holes, each said hole defined through the generally horizontal segment near a respective one of the two leg segments; positioning the plate against the bone; inserting a subchondral support element through the elongated slot defined through the generally horizontal segment of the plate and into the bone; and inserting at least two screws through the respective holes defined through the generally horizontal segment of the plate, and advancing each screw into the bone until a distal tip of each screw engages the subchondral support element.

Figure 14:
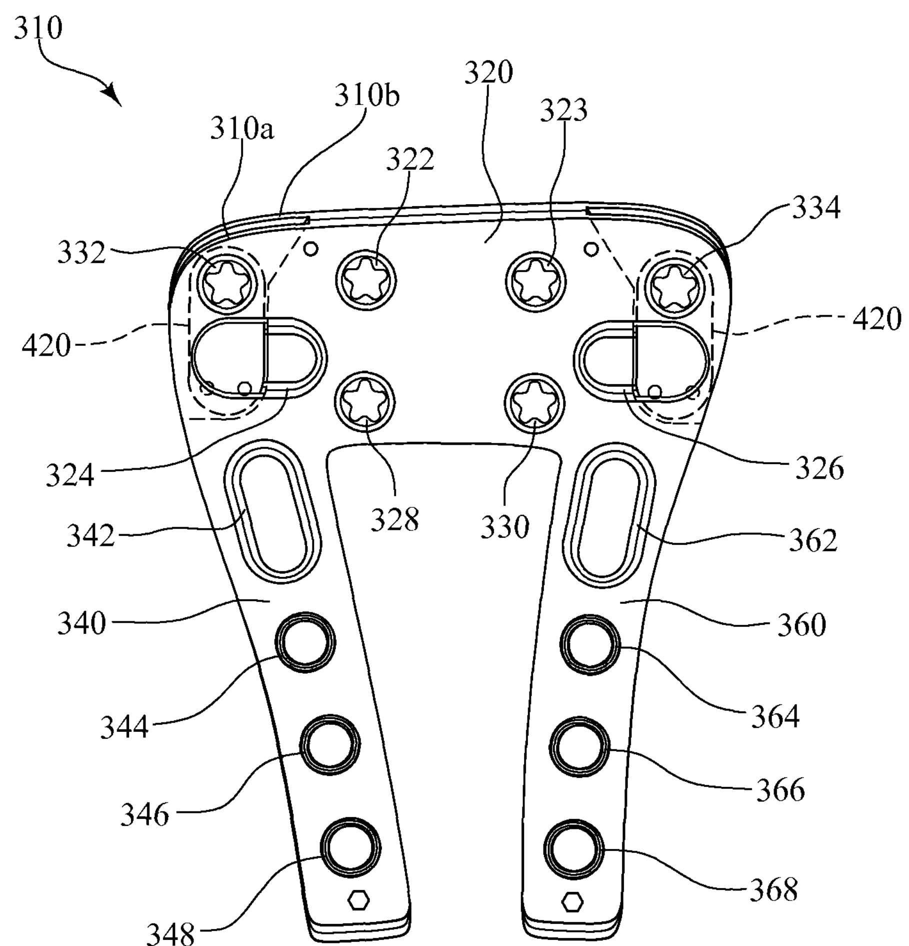
FIG. 14 is a view of another exemplary plate for use in the plate system of the present invention.

Referring now to FIG. 14, in another exemplary embodiment, the plate 310 again has a generally horseshoe-like shape with two leg segments 340, 360 extending downwardly from a generally horizontal segment 320. Again, such a shape with two columns keeps the central area of the bone (i.e., between the leg segments 340, 360) free and accessible. It is also believed that it is much easier to align the ends of the plate 310 to the edges of the bone, thereby obtaining a better centered construct. Furthermore, in this exemplary embodiment, the plate 310 is again comprised of two sections 310*a*, 310*b* that are joined together.

Referring still to FIG. 14, in this exemplary embodiment, there is no elongated slot defined through the center of the horizontal segment 320. Rather, there are two spaced variable angle locking holes 322, 323 in the first (or upper) row of the generally horizontal segment 320, near the center of the generally horizontal segment 320. There are also two spaced variable angle locking holes 328, 330 in the third (or lower) row of the generally horizontal segment 320.

Figure 15:
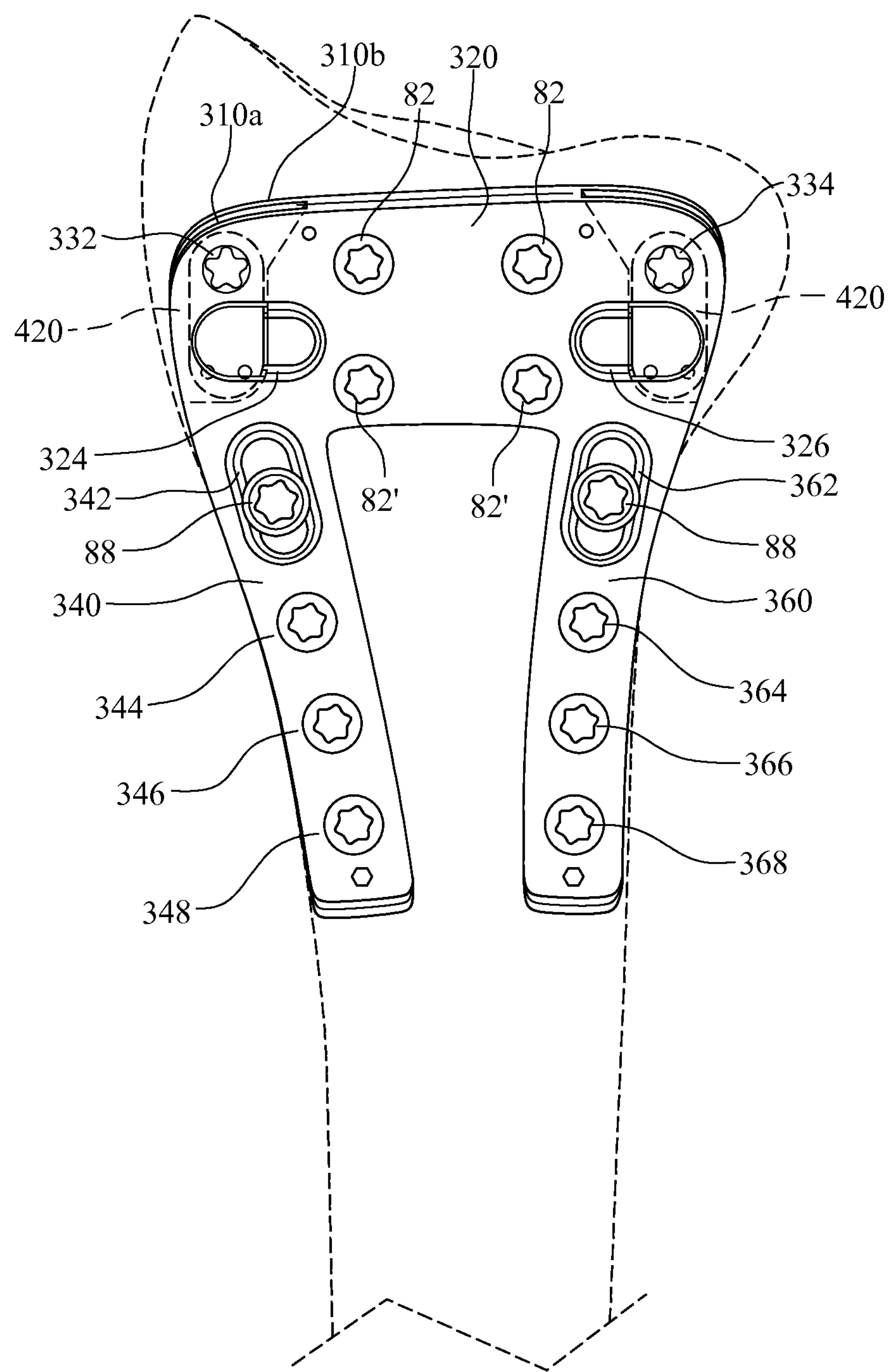
FIG. 15 is a view of the exemplary plate of FIG. 14 secured to a radius.
Figure 16:
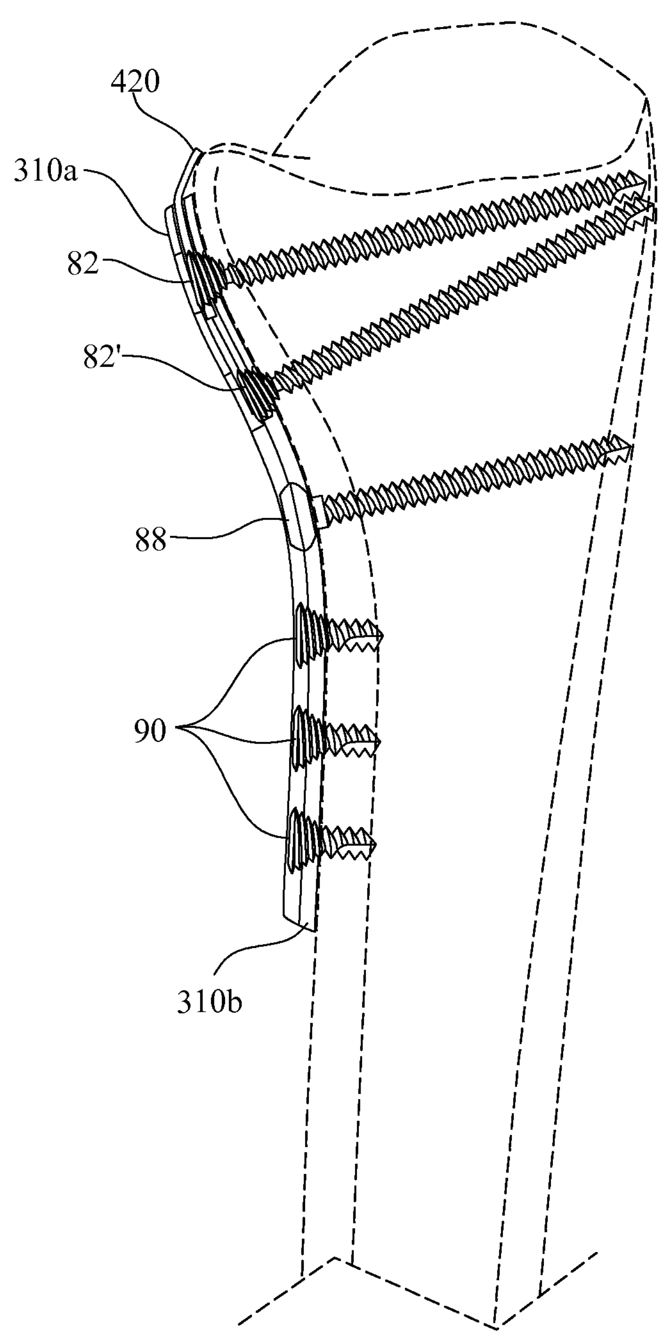
FIG. 16 is a side sectional view of the exemplary plate of FIG. 15 as secured to the radius.

Referring now to FIGS. 15-16, in some implementations and uses of the plate system of the present invention, the plate 310 is positioned against and secured to the distal radius (or other bone) to provide stability to a fracture. In this implementation, certain screws are again oriented to provide a "kickstand" subchondral support system. Specifically, a variable angle locking screw 82 is inserted into each of the variable angle locking holes 322, 323 in the first (or upper) row of the generally horizontal segment 320 of the plate 310, and then advanced into the bone. These two variable angle locking screws 82 serve as the subchondral support element. A second pair of variable locking screws 82' is inserted through each of the spaced variable angle locking holes 328, 330 in the third (or lower) row of the generally horizontal segment 320, and each variable angle locking screw 82' is advanced into the bone with the distal tip of each variable angle locking screw 82' converging toward and meeting the variable angle locking screw 82 above it. The result is that each variable locking screw 82 passing through the first (or upper) row of the generally horizontal segment 320 of the plate 310 meets with a variable locking screw 82' passing through the third (or lower) row of the generally horizontal segment 320 of the plate 310, thus providing the desired "kickstand" effect and a robust three-point and subchondral support.

Referring again to FIG. 14, the plate 310 also includes two additional variable angle locking holes 332, 334 in the first (or upper) row of the generally horizontal segment 320, one near the extreme radial (or left) edge of the plate 310 and one near the extreme ulnar (or right) edge of the plate 310. Each of these two variable angle locking holes 332, 334 can accommodate additional locking screws, if needed Referring still to FIG. 14, the plate 310 also includes two elongated slots 324, 326 in the second (or middle) row of the generally horizontal segment 320, one near the left edge of the plate 310 and one near the right edge of the plate 310. As discussed above with respect to FIGS. 11-12, such elongated slots 324, 326 can each receive a non-locking screw, which can be selectively covered by a respective rotating tab 420 in the down position, thus preventing the backing out of the non-locking screw and effectively converting it into a "pseudo" locking mode. In a second or up position, each rotating tab 420 can provide supplementary support to any ulnar or radial styloid fragment that may otherwise not be captured by the plate 310.

Referring still to FIG. 14, the plate 310 also includes an elongated slot 342 defined through and aligned with one leg segment 340, and there is an identical elongated slot 362 defined through and aligned with the other leg segment 360. Furthermore, there are threaded holes 344, 346, 348 defined through one leg segment 340 along the length of the leg segment 340, as well as threaded holes 364, 366, 368 defined through the other leg segment 360 along the length of the other leg segment 360.

Referring again to FIGS. 15-16, in some implementations and uses of the plate system of the present invention, non-locking screws 88 are inserted through each of the elongated slots 342, 362 aligned with the leg segments 340, 360 and then advanced into the bone. These non-locking screws 88 help secure the plate 310 to the bone and are used as the initial fixation screws. Also, having one locking screw 88 and associated elongated slot 342, 362 on either side makes it possible to fine tune the tilt and height of the plate 310 relative to the bone.

Finally, with respect to FIGS. 14-16, in some implementations and uses of the plate system of the present invention, a unicortical locking screw 90 is inserted into each of the threaded holes 344, 346, 348, 364, 366, 368 defined through the respective leg segments 340, 360 of the plate 310. Each of these unicortical locking screws 90 is locked into the plate 310 at a fixed angle. Furthermore, it is believed that using six unicortical locking screws 90, as opposed to fewer bicortical locking screws (as in prior art systems), will provide for similar strength; however, the advantage of unicortical locking screws is that there is less risk of dorsal structure irritation with mistakenly applied long screws. Moreover, there will be space for a plate and screws on the dorsal side should there be a need for that type of fixation.

Figure 17:
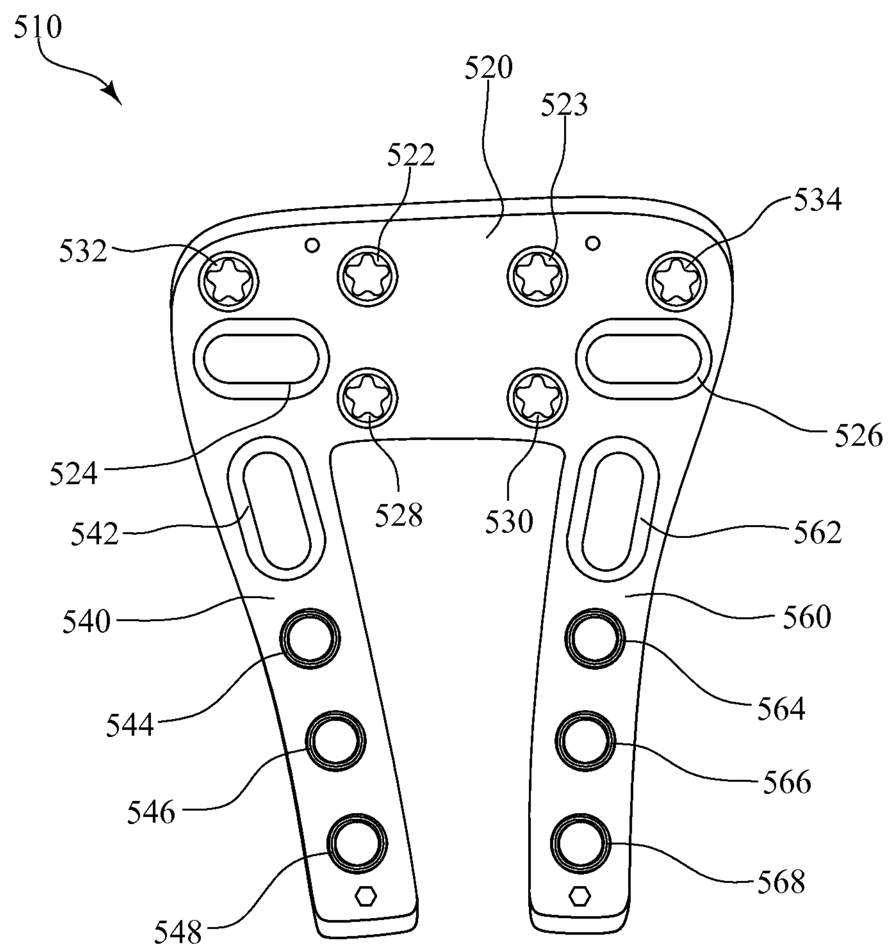
FIG. 17 is a view of another exemplary plate for use in the plate system of the present invention.

Referring now to FIG. 17, in another exemplary embodiment, the plate 510 is substantially identical to that described above with reference to FIGS. 14-16. For instance, the plate 510 again has a generally horseshoe-like shape with two leg segments 540, 560 extending downwardly from a generally horizontal segment 520. There are two spaced variable angle locking holes 522, 523 in the first (or upper) row of the generally horizontal segment 520, near the center of the generally horizontal segment 520. The plate 510 also includes two additional variable angle locking holes 532, 534 in the first (or upper) row of the generally horizontal segment 520, one near the extreme radial (or left) edge of the plate 510 and one near the extreme ulnar (or right) edge of the plate 510. There are also two spaced variable angle locking holes 528, 530 in the third (or lower) row of the generally horizontal segment 520. Furthermore, the plate 510 includes two elongated slots 524, 526 in the second (or middle) row of the generally horizontal segment 520, one near the left edge of the plate 510 and one near the right edge of the late 510. The plate 510 also includes an elongated slot 542 defined through and aligned with one leg segment 540, and there is an identical elongated slot 562 defined through and aligned with the other leg segment 560. Finally, there are threaded holes 544, 546, 548 defined through one leg segment 540 along the length of the leg segment 540, as well as threaded holes 564, 566, 568 defined through the other leg segment 560 along the length of the other leg segment 560. However, in this exemplary embodiment, the plate 510 is not comprised of multiple sections, but rather is a single, unitary plate. Accordingly, it does not include any rotating tabs that would interact with two elongated slots 524, 526 in the second (or middle) row of the generally horizontal segment 520 near the left and right edges of the plate 510.

Figure 18:
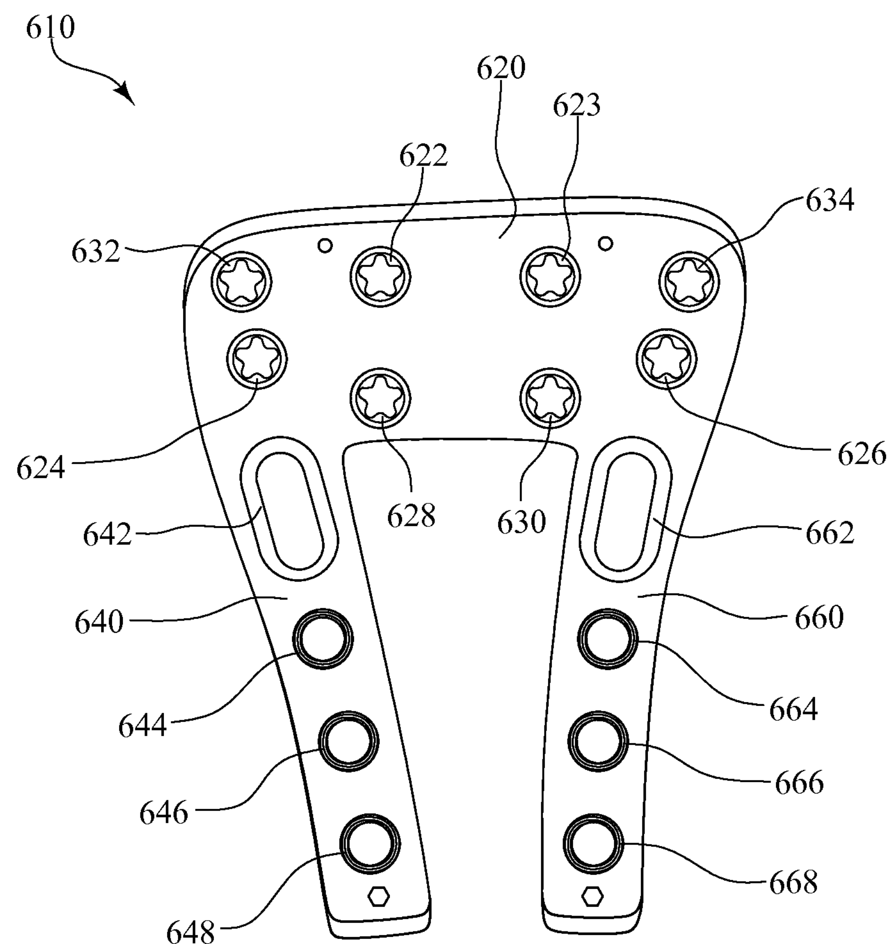
FIG. 18 is a view of another exemplary plate for use in the plate system of the present invention.

Referring now to FIG. 18, in another exemplary embodiment, the plate 610 is substantially identical to that described above with reference to FIG. 17. For instance, the plate 610 again has a generally horseshoe-like shape with two leg segments 640, 660 extending downwardly from a generally horizontal segment 620. There are two spaced variable angle locking holes 622, 623 in the first (or upper) row of the generally horizontal segment 620, near the center of the generally horizontal segment 620. The plate 610 also includes two additional variable angle locking holes 632, 634 in the first (or upper) row of the generally horizontal segment 620, one near the extreme radial (or left) edge of the plate 610 and one near the extreme ulnar (or right) edge of the plate 610. There are also two spaced variable angle locking holes 628, 630 in the third (or lower) row of the generally horizontal segment 320. The plate 610 also includes an elongated slot 642 defined through and aligned with one leg segment 640, and there is an identical elongated slot 662 defined through and aligned with the other leg segment 660. There are threaded holes 644, 646, 648 defined through one leg segment 640 along the length of the leg segment 640, as well as threaded holes 664, 666, 668 defined through the other leg segment 660 along the length of the other leg segment 660. However, in this exemplary embodiment, there are no elongated slots in the second (or middle) row of the generally horizontal segment 620. Rather, there are two additional variable angle locking holes 624, 626 in the second (or middle) row, one near the left edge of the plate 610 and one near the right edge of the plate 610.

One of ordinary skill in the art will recognize that additional embodiments and implementations are also possible without departing from the teachings of the present invention. This detailed description, and particularly the specific details of the exemplary embodiments and implementations disclosed therein, is given primarily for clarity of understanding, and no unnecessary limitations are to be understood therefrom, for modifications will become obvious to those skilled in the art upon reading this disclosure and may be made without departing from the spirit or scope of the invention.

What is claimed is:

1. A plate system for managing a fracture of a bone, comprising:
  a plate defining an elongated slot extending through the plate and at least two holes;
  a subchondral support element comprised of at least two screws, which, in use, is inserted through the elongated slot and advanced into the bone, and wherein each screw includes one or more paddles at its distal end defining an engagement surface; and
  at least two locking screws, which, in use, are each inserted into and locked into the respective holes, with each locking screw advancing into the bone such that a distal tip of each locking screw engages one of the engagement surfaces defined by a respective one of the at least two screws that comprise the subchondral support element.

2. A plate system for managing a fracture of a bone, comprising:
  a plate defining an elongated slot and at least two holes;
  a subchondral support element, which, in use, is inserted through the elongated slot and advanced into the bone, wherein said subchondral support element comprises a metal blade assembly including a substantially flat plate; and
  at least two locking screws, which, in use, are inserted into and locked into the respective holes, with each locking screw advancing into the bone such that a distal tip of each locking screw engages the subchondral support element.

3. The plate system as recited in claim 2, in which the substantially flat plate of the metal blade assembly terminates in a curved distal edge for receiving the distal tip of each locking screw.

4. A plate system for managing a fracture of a bone, comprising:
  a plate defining an elongated slot and at least two holes, and said plate further defining two additional elongated slots near its left and right edges, each additional elongated slot for accommodating a non-locking screw;
  a subchondral support element, which, in use, is inserted through the elongated slot and advanced into the bone; and
  at least two locking screws, which, in use, are inserted into and locked into the respective holes, with each locking screw advancing into the bone such that a distal tip of each locking screw engages the subchondral support element.

5. The plate system as recited in claim 4, wherein each of the two additional elongated slots includes a threaded portion which can accommodate another locking screw.

6. The plate system as recited in claim 4, wherein said plate further includes one or more rotating tabs, wherein, in use and in a down position, each rotating tab provides support for a non-locking screw received in one of the two additional elongated slots.

7. A plate system for managing a fracture of a bone, comprising:
  a plate defining an elongated slot and at least two holes, wherein said plate further has two leg segments extending downwardly from a generally horizontal segment, each of the two leg segments terminating in a free distal end;
  a subchondral support element, which, in use, is inserted through the elongated slot and advanced into the bone; and
  at least two locking screws, which, in use, are inserted into and locked into the respective holes, with each locking screw advancing into the bone such that a distal tip of each locking screw engages the subchondral support element.

8. A plate system for managing a fracture of a bone, comprising:
  a plate defining an elongated slot and at least two holes, wherein said plate further has two leg segments extending downwardly from a generally horizontal segment, and wherein said plate further includes (a) a first elongated slot defined through and aligned with one of the two leg segments for accommodating a non-locking screw and further having a threaded portion for accommodating a locking screw, and (b) a second elongated slot defined through and aligned with the other of the two leg segments for accommodating a non-locking screw, and further having a threaded portion for accommodating a locking screws;
  a subchondral support element, which, in use, is inserted through the elongated slot and advanced into the bone; and
  at least two locking screws, which, in use, are inserted into and locked into the respective holes, with each locking screw advancing into the bone such that a distal tip of each locking screw engages the subchondral support element.

9. A plate system for managing a fracture of a bone, comprising:
  a plate defining an elongated slot and at least two holes, wherein said plate further has two leg segments extending downwardly from a generally horizontal segment, with multiple threaded holes defined through each of the two leg segments along the length of each of the two leg segments;
  a subchondral support element, which, in use, is inserted through the elongated slot and advanced into the bone;
  at least two locking screws, which, in use, are inserted into and locked into the respective holes, with each locking screw advancing into the bone such that a distal tip of each locking screw engages the subchondral support element; and
  multiple unicortical locking screws, which, in use, are inserted into the threaded holes and locked to said plate, while also engaging the bone.

10. A plate system for managing a fracture of a bone, comprising:
  a plate with two leg segments extending downwardly from a generally horizontal segment, said plate including
    an elongated slot defined through the generally horizontal segment near its top edge, with variable angle locking holes at either end of the elongated slot, and
    two holes, each said hole defined through the generally horizontal segment near a respective one of the two leg segments;
  at least two paddle screws, which, in use, are inserted into and locked into the respective variable angle locking holes at either end of the elongated slot, with each of the paddle screws advancing into the bone; and at least two screws, which, in use, are inserted into the respective holes, with each screw advancing into the bone with a distal tip of each screw engaging a distal end of a respective paddle screw, thus providing a three-point support.

11. The plate system as recited in claim 10, wherein said plate further includes two additional elongated slots defined through the generally horizontal segment near its left and right edges, each additional elongated slot for accommodating a non-locking screw.

12. The plate system as recited in claim 11, wherein each of the two additional elongated slots includes a threaded portion which can accommodate another locking screw.

13. The plate system as recited in claim 11, wherein said plate further includes one or more rotating tabs, wherein, in use and in a down position, each rotating tab provides support for a non-locking screw received in one of the two additional elongated slots.

14. The plate system as recited in claim 10, wherein said plate further includes a first elongated slot defined through and aligned with one of the two leg segments for accommodating a non-locking screw and further having a threaded portion for accommodating a locking screw; and a second elongated slot defined through and aligned with the other of the two leg segments for accommodating a non-locking screw, and further having a threaded portion for accommodating a locking screw.

15. The plate system as recited in claim 10, wherein said plate further includes multiple threaded holes defined through each of the two leg segments along the length of each of the two leg segments, and further comprising multiple unicortical locking screws, which, in use, are inserted into the threaded holes and locked to said plate, while also engaging the bone.

16. A plate system for managing a fracture of a bone, comprising:

a plate with two leg segments extending downwardly from a generally horizontal segment, said plate including an elongated slot defined through the generally horizontal segment near its top edge, and two holes, each said hole defined through the generally horizontal segment near a respective one of the two leg segments;

a metal blade assembly including a substantially flat plate that terminates in a distal edge, wherein, in use, the substantially flat plate is inserted through the elongated slot and advances into the bone; and at least two screws, which, in use, are inserted into the respective holes, with each screw advancing into the bone with a distal tip of each screw engaging the distal edge of the substantially flat plate of the metal blade assembly, thus providing a three-point support.

17. The plate system as recited in claim 16, wherein the distal edge of the substantially flat plate of the metal blade assembly is curved.

18. The plate system as recited in claim 16, wherein said plate further includes two additional elongated slots defined through the generally horizontal segment near its left and right edges, each additional elongated slot for accommodating a non-locking screw.

19. The plate system as recited in claim 18, wherein each of the two additional elongated slots includes a threaded portion which can accommodate another locking screw.

20. The plate system as recited in claim 18, wherein said plate further includes one or more rotating tabs, wherein, in use and in a down position, each rotating tab provides support for a non-locking screw received in one of the two additional elongated slots.

21. The plate system as recited in claim 16, wherein said plate further includes a first elongated slot defined through and aligned with one of the two leg segments for accommodating a non-locking screw and further having a threaded portion for accommodating a locking screw; and a second elongated slot defined through and aligned with the other of the two leg segments for accommodating a non-locking screw, and further having a threaded portion for accommodating a locking screw.

22. The plate system as recited in claim 16, wherein said plate further includes multiple threaded holes defined through each of the two leg segments along the length of each of the two leg segments, and further comprising multiple unicortical locking screws, which, in use, are inserted into the threaded holes and locked to said plate, while also engaging the bone.

23. A plate for use in managing a fracture of a bone, comprising:

a generally horizontal segment that can be characterized as having at least an upper row and a lower row;

two leg segments extending downwardly from the generally horizontal segment each of the two leg segments terminating in a free distal end;

at least two spaced holes in the upper row of the generally horizontal segment, each said hole in the upper row for accommodating a locking screw; and at least two spaced holes in the lower row of the generally horizontal segment, each said hole in the lower row for accommodating a locking screw.

24. The plate as recited in claim 23, in which each said hole in the upper row is a variable angle locking hole.

25. The plate as recited in claim 23, in which each said hole in the lower row is a variable angle locking hole.

26. The plate as recited in claim 24, and further comprising two additional variable angle locking holes in the upper row of the generally horizontal segment, one near a left edge of the plate and one near a right edge of the plate, each additional variable angle locking hole for accommodating a locking screw.

27. The plate as recited in claim 23, and further comprising two elongated slots in a middle row of the generally horizontal segment, one near a left edge of the plate and one near a right edge of the plate, each elongated slot for accommodating a non-locking screw.

28. The plate as recited in claim 23, and further comprising two additional variable angle locking holes in a middle row of the generally horizontal segment, one near a left edge of the plate and one near a right edge of the plate, each additional variable angle locking hole for accommodating a non-locking screw.

29. The plate as recited in claim 23, and further comprising a first elongated slot defined through and aligned with one of the two leg segments for accommodating a non-locking screw, and a second elongated slot defined through and aligned with the other of the two leg segments for accommodating a non-locking screw.

30. The plate as recited in claim 23, and further comprising multiple threaded holes defined through each of the two leg segments along the length of each of the two leg segments, each said threaded hole for accommodating a unicortical locking screw.

* * * * *